United States Patent [19]

Hoff et al.

[11] 4,197,361

[45] Apr. 8, 1980

[54] FLUORESCENT IMMUNOASSAY SANDWICH TECHNIQUE FOR HB$_s$AG

[75] Inventors: Gail Hoff, Millington; Lillian Robichaud, Long Valley, both of N.J.

[73] Assignee: Warner-Lambert, Morris Plains, N.J.

[21] Appl. No.: 827,187

[22] Filed: Aug. 23, 1977

[51] Int. Cl.$^2$ .................... G01N 21/52; G01N 31/00; G01N 31/22; G01N 33/16
[52] U.S. Cl. ...................... 424/8; 23/230 B; 424/12; 424/13; 435/7
[58] Field of Search ................ 424/1, 8, 12, 13, 86, 424/89; 195/103.5 A; 23/230 B, 253 TP

[56] References Cited

U.S. PATENT DOCUMENTS

| | | | |
|---|---|---|---|
| 3,992,631 | 11/1976 | Harte | 424/12 |
| 3,999,948 | 12/1976 | Deindoerfer | 424/8 X |
| 4,011,308 | 3/1977 | Giaever | 424/8 X |
| 4,025,310 | 5/1977 | Bolz | 424/12 X |
| 4,036,946 | 7/1977 | Kleinerman | 424/8 |
| 4,041,146 | 8/1977 | Giaever | 424/7 |

*Primary Examiner*—Anna P. Fagelson
*Attorney, Agent, or Firm*—George M. Kaplan; Albert H. Graddis

[57] ABSTRACT

An immunoassay for the sandwich technique is disclosed in which antibody (or antigen) is bound to a plastic strip, and after reaction with a test sample and then fluorescently tagged antibody (or antigen), fluorescense is read directly from the plastic strip in a fluorometer.

5 Claims, No Drawings

FLUORESCENT IMMUNOASSAY SANDWICH TECHNIQUE FOR HB$_s$AG

Since the discovery of Australia Antigen by Blumberg in 1963, research on the pathogenesis of hepatitis has mushroomed. Viral and serum hepatitis, traditionally differentiated by their respective incubation periods and routes of transmission, are known to be caused by distinct viruses, hepatitis A (HA) and hepatitis B (HB), with overlapping incubation periods and routes of transmission. The HB virus has an antigen on its surface coat that is called hepatitis B surface antigen (HB$_s$Ag), formerly Australia Antigen (Au) or Hepatitis Associated Antigen (HAA). Because excess HB$_s$Ag is often produced in the cytoplasm of the liver cells and secreted into the blood, detection and epidemiologic knowledge of HB is more extensive than of the more elusive HA.

In the developed countries, parenteral drug use, commercial blood banks, and increased blood transfusions created alarming increases in the incidence of HB, whereas in underdeveloped countries, sanitary conditions contributed to the high incidence. As estimated 100 million chronic carriers of HB$_s$Ag create a world health problem, and research has been keen on enhancing and simplifying methods of detection.

Both HA and HB have been detected in vitro immunologically. Antibody to a viral component binds with that component and produces an antigen-antibody complex. If present in large amounts and in optimal proportions, a visible precipitate forms, and early methods of detection (gel diffusion and counterelectrophoresis (CEP)) depended on seeing a band of this precipitate in gel.

A radioimmunoassay for HB$_s$Ag was introduced in 1973 and the sensitivity for detecting HB$_s$Ag was increased 200 fold over CEP.

Although a great improvement over CEP, there are reports of false positives. Most were due to errors in technique, but a few sera also reacted with the guinea pig globulin used for antibody, causing false positives. There were also false negatives. Even with RIA, nearly 50% of the infectious units of blood for transfusion were missed.

In 1974 an improved system was introduced and substituted a roughened polystyrene bead for the test tube used in the original test. The radioactive labelled anti-HB$_s$ was changed from guinea pig origin to human origin, purportedly reducing some false positive reactions. The new system also had fewer errors of technique. Sensitivity was increased slightly, and a confirmatory test was also made available.

Recently, two additional RIA kits for HB$_s$Ag have been introduced. One has a double bead and uses human anti-HB$_s$ for both the antibody on the solid phase and the $^{125}$I labelled antibody. The other test uses controlled pore glass particles coated with goat anti-HB$_s$ in tablet form and $^{125}$I labelled goat anti-HB$_s$ for the tracer antibody.

Several hemagglutination systems are also available. One has guinea pig antibody attached to a fixed human erythrocyte. Another uses horse antibody on a fixed turkey erythrocyte, and still another uses sheep cells. These antibody coated cells agglutinate in the presence of HB$_s$Ag. Although these systems do not require expensive equipment and are easy to perform, they have more false positives and are less sensitive than RIA.

We have now developed an immunoassay system which can detect HB$_s$Ag with great sensitivity and specificity while eliminating the inconveniences of RIA, using the sandwich technique.

The ability of proteins to absorb to plastic materials is a well known phenomenon and the basis for the sandwich technique employed in immunology to quantitate antigens contained in solution.

In the sandwich technique, immunologically reactive antibody adsorbed to a plastic stock material, called a solid phase antibody, will bind antigen. If this bound antigen is multivalent and thus has additional reactive sites for antibody, an antibody which has previously been labelled with a quantitative tag such as radioactive isotope or enzyme can provide an index of the amount of antigen bound to the solid phase. The technique is also capable of use when an immunologically reactive antigen is first absorbed to the plastic stock material.

The concept of this technique is of using a solid strip as a matrix for solid phase antibody, submerging the strip in antigen followed by fluorochrome labelled antibody, and reading bound fluorescent antibody directly from the solid phase in a spectrophotofluorometer. By the term fluorochrome is meant fluorescent compounds among which are fluorescein, rhodamine, or their salts.

We have now developed a novel immunoassay for multivalent antigens, where sensitivity and specificity are paramount and the inconveniences of radioimmunoassay could be eliminated, which is directed towards a fluorescent immunoassay using the sandwich technique. This development can be designed to also allow pre-absorbed antigen to detect multivalent antibody within the test solution.

Flat, solid strips of low fluorescence acrylic plastic 0.31 inches in width were used as the solid phase for absorbed antibody in the sandwich technique. These strips were sized to fit diagonally within the cuvette holder of a conventional spectrophotometer. Each strip is read for background fluorescence prior to testing.

Because it was unknown what optical effect a smooth or rough surface would have on fluorescence, sandblasted and smooth acrylic strips were compared under identical conditions, using both direct adsorption of antigen (i.e. solid phase not solid phase antibody) as well as the sandwich technique. The antigen used was human $\gamma$ globulin, and fluoroscein isothiocyanate labelled anti-human $\gamma$ globulin was the indicator. Sandblasted strips produced a higher signal and showed greater sensitivity in the systems that smooth strips in both the sandwich technique and for antigen bound directly by adsorption. The results were determined by subtracting background fluorescence of control strips from fluorescence of strips exposed to antigen and FITC labelled antibody; results obtained by dividing the fluorescence of strips exposed to antigen by background fluorescence are similar.

After reading fluorescence of sandblasted strips incubated for 15 minutes at 56° in labelled antibody, strips which bound antigen by antibody (the sandwich technique) were incubated in the labelled antibody for an additional 18 hours at room temperature. The sensitivity increased with increased incubation time. However, if incubation extended for too long a period of time (5 days at 4° C.), non-specific binding of fluorescent antibody obscured detection of lower levels of antigen.

The novel technique of this invention generally comprises cleaning these strips first with a petroleum ether and then with a non-ionic detergent after which they are absorbed with antiserum containing sufficient specific antibody to detect corresponding antigen. After a sufficient time for absorption of the antibody onto the solid phase, the solid phase antibody strips are immersed in an antigen containing solution (the sample) for the binding of corresponding antigen at the immunologically reactive sites on the antibody molecule. The solid phase antibody along with any bound antigen is then immersed in a solution containing antibody labeled with a fluorochrome. The strips are then placed, without the requirement of centrifugation to separate bound from free antibody, diagonally in the cuvette holder of a spectrofluorometer containing the appropriate filters to reduce or eliminate extraneous fluorescence from the plastic, non-specifically bound proteins and excitation light. Specific fluorescence from the fluorescently labeled antibody has been found to be proportional to the antigen concentration providing the solid phase has been washed free of un-bound proteins between each operation.

This technique has been specifically used to detect hepatitis B antigen ($HB_sAg$) using the following method of Example 1:

EXAMPLE 1

A sheet of polymethyl methacrylate 0.31 inches thick and sandblasted on one side with steel grit to increase the surface area, was cut into strips 0.80 by 0.67 inches to fit diagonally into the cuvette holder of a spectrofluorometer. The solid phase was washed with petroleum ether, 2% Triton X-100 (aqueous), and after washing in water was incubated at 56° C. for two hours in sheep anti-$HB_s$ which had a titre of 1:8 by counter-electrophoresis with a $HB_sAg$ sample that had a titre of 1:10,000 by radioimmunoassay. Each strip was then read for background fluorescence and then incubated with 1.75 ml of a $HB_sAg$ positive serum (having a titre of 1:10,000 by radioimmunoassay) or its dilutions in serum negative by radioimmunoassay for $HB_sAg$ or anti-$HB_s$ for 17 to 20 hours at room temperature. Control strips were also prepared wherein the strip was incubated with 1.75 ml of normal human serum being negative for $HB_sAg$. After washing the strips were incubated in 1.75 ml of fluoroscein labeled Sheep anti-$HB_s$ (prepared in accordance with the method of D. M. Weir, Handbook of Experimental Immunology, 2nd Edition, Blackwell Scientific Publications, Oxford, 1974, p. 18.6 et seq.) and incubated for 15 minutes at 56° C. or 6 days at 4° C. The strips were washed before each operation. The strips were then allowed to dry and were then placed diagonally into the cuvette holder of the spectrofluorometer with the smooth surface facing the excitation light and read at 473 m$\mu$ excitation and 520 m$\mu$ emission wavelength for specific fluorescence. An American Optical 2070-617 blue interference filter and a Schott OG 515 barrier filter were used to reduce or eliminate extraneous fluorescence.

The amount of fluorescently labeled antibody bound to the solid phase by antigen as prepared in Example 1, after subtraction of background fluorescence from the solid phase material and of non-specific fluorescence of the $HB_sAg$ negative controls, is proportional to the antigen concentration and the sensitivity for detecting $HB_sAg$ is comparable to that found by radioimmunoassay without the disadvantages of RIA techniques.

The sandwich technique according to this example can also be reversed in design so that preadsorbed antigen can detect multivalent antibody which would then be quantitated with a fluorochrome labeled antibody.

The system can also be modified to allow detection and quantitation of antigens by direct adsorption to the solid phase using a fluorochrome labeled antigen.

This system can also be modified to allow detection and quantitation of antigens by direct adsorption to the solid phase using a fluorochrome labeled antibody. This method has been specifically used to detect gamma globulin (IgG).

EXAMPLE 2

Sandblasted plastic strips sized and cleaned as described in Example 1 were incubated at 56° C. for one hour in 7 ml of varying human gamma globulin concentrated solutions (0.001-10 mg/ml) diluted with 2% bovine serum albumin. After washing each strip was then read for background fluorescence and then incubated in 2 ml of commercial fluorescein labeled goat antihuman gamma globulin which had an O.D. at 280/495 ratio of 1.1, and which had been diluted 1 to 7 in saline. After incubation for 15 minutes at 56° C., the strips were washed, placed in the fluorometer and read at 473 m$\mu$ excitation and 520 m$\mu$ emission wavelength for specific fluorescence.

The amount of specific fluorescence seen in Example 2 is proportional to the concentration of gamma globulin solution. Sensitivity utilizing the method of Example 2 is approximately 0.01 mg gamma globulin per mil.

This system can also be modified to allow detection and quantitation of antibody by direct absorption to the solid phase using a fluorochrome labeled antigen.

We claim:

1. A method for performing an immunoassay to detect hepatitis B surface antigen which comprises:
   A. Thoroughly cleaning a solid phase plastic component which is sized to fit diagonally into the cuvette holder of a spectrofluorometer capable of adsorbing antibody to $HB_sAg$;
   B. Sandblasting the plastic component to increase the surface area;
   C. Incubating the cleaned solid phase component at 56° C. for about two hours with an antibody specific to $HB_sAg$;
   D. Washing the solid phase antibody to remove extraneous nonreacted antibody;
   E. Placing the washed solid phase antibody into a spectrofluorometer and obtaining a reading for background fluorescence;
   F. Incubating the solid phase antibody in a solution containing an unknown quantity of $HB_sAg$ at room temperature for a time sufficient for an immunological reaction to occur;
   G. Washing the reacted solid phase antibody to remove extraneous nonreacted antigen;
   H. Incubating the washed solid phase antibody-antigen with a fluorochrome labeled antibody specific to $HB_sAg$;
   I. Washing the fluorochrome labeled solid phase to remove extraneous nonreacted labeled antibody; and
   J. Determining the amount of fluorescently labelled antibody bound to the solid phase antibody-antigen by determining the increased amount of fluorescence over the background fluorescence, which increased fluorescence is proportional to the $HB_sAg$ concentration in the test solution.

2. The method of claim 1 which further comprises preparing of a negative control by employing as the solution of step E of said method a normal human serum solution, which is negative for $HB_sAg$; determining any-non-specific fluorescence of said control prior to step H, and in step J determining increased fluorescence over background and non-specific fluorescence.

3. The method of claim 1 wherein the plastic component is in the form of a strip, which after step I, is allowed to dry and placed diagonally into the cuvette holder of the spectroflurometer with the smooth surface facing the excitation light.

4. The method according to claim 1 wherein the fluorochrome is fluoroscein.

5. The method of claim 4 wherein the fluoroscein labeled antibody and solid phase antibody-antigen are incubated for about 15 minutes at 56° C. or six days at 4° C.

* * * * *